(12) United States Patent
Boire et al.

(10) Patent No.: US 12,376,856 B1
(45) Date of Patent: Aug. 5, 2025

(54) SYNTHETIC PERIVASCULAR WRAP

(71) Applicants: Timothy Boire, Houston, TX (US); Natacha Rodrigues, Houston, TX (US); Colin Dodson, Houston, TX (US); Steven M. Tallman, Jr., Houston, TX (US); Nick Sears, Houston, TX (US); Bryan Khai Ngo, Houston, TX (US); Laura Rose Emerson, Houston, TX (US); Geoffrey A Lucks, Houston, TX (US)

(72) Inventors: Timothy Boire, Houston, TX (US); Natacha Rodrigues, Houston, TX (US); Colin Dodson, Houston, TX (US); Steven M. Tallman, Jr., Houston, TX (US); Nick Sears, Houston, TX (US); Bryan Khai Ngo, Houston, TX (US); Laura Rose Emerson, Houston, TX (US); Geoffrey A Lucks, Houston, TX (US)

(73) Assignee: Venostent, Inc., Houston, TX (US)

( * ) Notice: Subject to any disclaimer, the term of this patent is extended or adjusted under 35 U.S.C. 154(b) by 764 days.

(21) Appl. No.: 17/383,431

(22) Filed: Jul. 22, 2021

Related U.S. Application Data

(60) Provisional application No. 63/055,335, filed on Jul. 23, 2020.

(51) Int. Cl.
*A61B 17/11* (2006.01)
*A61B 8/08* (2006.01)
*A61B 17/00* (2006.01)

(52) U.S. Cl.
CPC .............. *A61B 17/11* (2013.01); *A61B 8/085* (2013.01); *A61B 2017/00871* (2013.01);
(Continued)

(58) Field of Classification Search
CPC ............ A61B 17/11; A61B 2017/1103; A61B 2017/1107; A61B 8/085; A61B 2017/1135; A61B 2017/1139
See application file for complete search history.

(56) References Cited

U.S. PATENT DOCUMENTS

| 2006/0052866 A1* | 3/2006 | Gilles | .............. A61B 17/12013 623/1.51 |
| 2010/0114292 A1* | 5/2010 | Heaton | .................... A61F 2/064 623/1.36 |

(Continued)

*Primary Examiner* — Darwin P Erezo
*Assistant Examiner* — Christina C Lauer
(74) *Attorney, Agent, or Firm* — Patterson Intellectual Property Law, P.C.; Seth R. Ogden; Mark A. Kilgore

(57) ABSTRACT

In one aspect of the present disclosure, devices and methods of treating a vascular anastomosis is disclosed. In one embodiment, the method comprises the steps of: (a) determining the outer diameter of a first vessel to be surgically coupled to a second vessel creating a vascular anastomosis; (b) determining the outer diameter of the second vessel; (c) selecting a perivascular wrap from a plurality of differently sized perivascular wraps such that the perivascular wrap fits around the vascular anastomosis with a constriction of the first vessel of less than 30%; wherein the perivascular wrap includes a shape memory polymer and has at least a first end, a second end, and a medial region; (d) positioning the perivascular wrap onto the first vessel via the first end prior to construction of the vascular anastomosis; (e) coupling the first vessel and the second vessel constructing the vascular anastomosis; and (f) molding the perivascular wrap from a first shape to a second shape wherein the second shape conforms to the geometry of the vascular anastomosis such that the perivascular wrap provides artery-mimetic support to the vascular anastomosis in the range of 0.1-2.0 MPa.

18 Claims, 19 Drawing Sheets

(52) U.S. Cl.
CPC ............. *A61B 2017/1107* (2013.01); *A61B 2017/1135* (2013.01); *A61B 2017/1139* (2013.01)

(56) References Cited

U.S. PATENT DOCUMENTS

| | | | |
|---|---|---|---|
| 2010/0280598 A1* | 11/2010 | Fox | A61F 2/064 623/1.32 |
| 2015/0119908 A1* | 4/2015 | Consigny | A61M 1/3655 606/156 |
| 2020/0297899 A1* | 9/2020 | Boire | A61L 31/06 |

* cited by examiner

SYNTHETIC PERIVASCULAR WRAP

CROSS-REFERENCES TO RELATED APPLICATIONS

This application claims benefit of the following patent application(s) which is/are hereby incorporated by reference: 63/055,335 filed on Jul. 23, 2020

STATEMENT REGARDING FEDERALLY SPONSORED RESEARCH OR DEVELOPMENT

This invention was made with government support under Grant Number 1927086 awarded by the National Science Foundation. The government may have certain rights in the invention.

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

REFERENCE TO SEQUENCE LISTING OR COMPUTER PROGRAM LISTING APPENDIX

Not Applicable

BACKGROUND SUMMARY

The present disclosure relates generally to medical devices, systems, and methods. More particularly, this disclosure pertains to extravascular support devices, such as perivascular wraps, stents, support devices, and the like, for treatment of vascular diseases or injuries, such as arteriovenous fistulas (AVFs), arteriovenous grafts (AVGs), or centralized venous catheters (CVCs). AVFs are direct artery-vein connections surgically created in the arm, the three most common of which are the radiocephalic (radial artery to cephalic vein) forearm fistula, brachiocephalic (brachial artery to cephalic vein) upper arm fistula, and the brachial artery-to-transposed basilic vein upper arm fistula. For AVGs, grafts (typically expanded polytetrafluoroethylene (ePTFE) or GORETEX®) are superficially tunneled underneath the skin of the arm to connect a vein to an artery and allow for easy cannulation. This is done in either a straight or looped configuration, and most commonly involves connecting the brachial artery to cephalic vein in the antecubital fossa, or the brachial or axillary artery to the brachial or axillary vein. CVCs are catheters connected to the jugular, femoral, or subclavian vein. These vascular procedures are commonly used in patients undergoing hemodialysis for end-stage renal disease (ESRD). Hemodialysis is by far the most prevalent form of dialysis and treatment for ESRD patients, and serves as the primary lifeline for most ESRD patients.

End-stage renal disease (ESRD) is Stage 5, the final stage, of chronic kidney disease, in which the kidneys are less than 10% functional or completely non-functional. Patients with ESRD experience a variety of symptoms, including difficulty or a complete inability to urinate, fatigue, headaches, nausea, vomiting, malaise, loss of appetite, inexplicable weight loss, dry skin, extreme bruising, bad breath, numbness on hands and feet, excessive thirst, frequent hiccups, impotence, absence of menstrual cycles, sleep issues, and edema. An extensive list of potential complications of ESRD exist and can include skin infection from dry and itchy skin, other infections, joint, bone and muscle pain, weak bones, and nerve damage. Less common but still serious complications include malnutrition, anemia, cardiovascular issues, vascular disorders, pulmonary embolisms, intestinal bleeding, dementia, seizures, fractures, joint disorders, hyperparathyroidism, and liver failure. Proper dieting and use of medication can alleviate some of these symptoms, but ESRD is a life-threatening disorder with overall 5-year survival rates of approximately 54%.

In order to sustain life, kidney function needs to be restored by kidney transplant or replaced by dialysis treatments. Due to the lack of available and viable kidney transplants for the vast number of patients with ESRD, as well as the operative mortality risk for many patients due to comorbid conditions (e.g., cardiac, pulmonary, or peripheral vascular disease/issues), transplants are often not a feasible option; thus, dialysis is the primary mode of treatment for 87% of incident ESRD patients and 63% of prevalent patients. The two general options for dialysis are hemodialysis, in which blood is filtered externally and returned to the body clean three times per week for four hours at a time, and peritoneal dialysis, in which a solution placed in the abdomen is frequently removed via a catheter. The most common form of dialysis for these patients is hemodialysis which may include the use of vascular surgeries as noted previously.

For hemodialysis treatments, AVFs and AVGs are preferred to CVCs as they are far less prone to bacteremia, sepsis, thrombosis, central venous stenosis, and death. Between AVFs and AVGs, AVFs are often preferred over AVGs because they tend to last longer, have less complications from thrombosis, require fewer interventions at a lower cost, have lower infection and steal syndrome rates, lower central venous stenosis, and have 20% lower mortality rates. Under the guidance of the Center for Medicare & Medicaid Services' (CMS') Quality Incentive Program (QIP), the Fistula First Catheter Last (FFCL) Workgroup Coalition, the Kidney Disease Outcomes Quality Initiative, and the Kidney Disease Improving Global Outcomes clinical practice guidelines, the use of AVFs has nearly doubled since 2003 resulting in approximately 67% of current hemodialysis patients using an AVF. Untreated AVFs are thus considered the current standard of care for hemodialysis and ESRD patients.

Although AVFs are the current standard of care for hemodialysis and ESRD patients, 39% of surgically-created fistulas fail to mature, or even be used for dialysis in the first place. To make matters worse, if balloon angioplasty or intraluminal stenting is required to help assist with maturation of the surgical site or surrounding area, patients are at a significantly greater risk of patency loss post-maturation. Of those that do mature, maturation takes an average of 120 days, and 40% of them fail within one year—an overall failure rate of 55%-65% within a year. As a result of this failure-prone and slow maturation process, and subsequent patency loss, many patients are forced to rely on CVCs for extended periods of time; in fact, 80% of ESRD patients still initiate hemodialysis on a catheter, and central venous stenosis in CVCs can preclude future use of AVFs or AVGs. Currently, there are no approved or cleared products in the US that can prophylactically treat fistulas and/or grafts to reduce reliance on infection-, mortality-, and complication-prone CVCs and obviate or dissipate this precarious, life-threatening situation for ESRD patients.

The primary reason why AVFs and AVGs fail is venous stenosis caused by neointimal hyperplasia as well as lack of positive (i.e. outward) remodeling of the vasculature.

Neointimal hyperplasia is the process by which vascular smooth muscle cells (VSMCs) and myofibroblasts within vein walls migrate inwards toward the intima, proliferate, and deposit extracellular matrix proteins that form a "neointima"; the neointima obstructs blood flow through the access site and either interventions to combat the formation of the neointima must be used or the neointima forces abandonment of the access site. Additionally, arteries and veins have different mechanical properties—arteries are stiffer and thicker than veins and are far better equipped to withstand the high pressures and flow rates of the arterial environment. The difference in mechanical properties between arteries and veins (i.e. leads to compliance mismatch) and exposure of the vein to an order of magnitude increase in pressure and flow from AVF/AVG creation cause heightened vein wall tension and radial stresses, turbulence, and stenotic wall shear stresses (WSSs) (low, oscillating as well as high WSSs). The net effect is that in AVFs and AVGs, the exposed vein maladapts to the new vasculature environment by thickening its walls inwardly via neointimal hyperplasia, causing stenosis and obstructing blood flow through the access site that results in failures of both maturation and patency and ultimately failure of the AVF/AVG.

What is needed, then, is new devices, systems, and methods for treating vascular diseases or injuries, such as arteriovenous fistulas (AVFs), arteriovenous grafts (AVGs), or centralized venous catheters (CVCs), which results in much better clinical outcomes for patients. It would be desirable to develop devices and methods for reducing neointimal hyperplasia, for supporting the vasculature at a surgical site to induce outward remodeling and not inward remodeling, and to reduce overall vein wall tension and radial stress as a result of increased blood pressure and flow. Additionally, it would be desirable to develop devices and methods for increasing maturation and patency of surgical procedures to reduce the failure rates in patients as well as reduce the need for healthcare providers to use other interventions to help assist with maturation of the surgical site or surrounding area.

BRIEF SUMMARY

In one aspect of the present disclosure, a method of treating a vascular anastomosis is disclosed, the method comprising the steps of: (a) determining the outer diameter of a first vessel to be surgically coupled to a second vessel creating a vascular anastomosis; (b) determining the outer diameter of the second vessel; (c) selecting a perivascular wrap from a plurality of differently sized perivascular wraps such that the perivascular wrap fits around the vascular anastomosis with a constriction of the first vessel of less than 30%; wherein the perivascular wrap includes a shape memory polymer and has at least a first end, a second end, and a medial region; (d) positioning the perivascular wrap onto the first vessel via the first end prior to construction of the vascular anastomosis; (e) coupling the first vessel and the second vessel constructing the vascular anastomosis; and (f) molding the perivascular wrap from a first shape to a second shape wherein the second shape conforms to the geometry of the vascular anastomosis such that the perivascular wrap provides artery-mimetic support to the vascular anastomosis in the range of 0.1-2.0 MPa.

In one embodiment, the method may further include wherein the vasculature comprises a vein and an artery.

In one embodiment, the method may further include wherein the vasculature comprises a graft.

In one embodiment, the method may further include wherein the determining step of (a) includes measuring the outer diameter via ultrasound.

In one embodiment, the method may further include wherein the determining step of (b) includes measuring the outer diameter via ultrasound.

In one embodiment, the method may further include determining the inner diameter of the first vessel.

In one embodiment, the method may further include determining the inner diameter of the second vessel.

In one embodiment, the method may further include the shape memory polymer comprises poly (ε-caprolactone).

In one embodiment, the method may further include the shape memory polymer comprises poly (ε-caprolactone)-co-(α-allyl carboxylate ε-caprolactone).

In one embodiment, the method may further include the molding of the perivascular wrap is formed to have direct contact with the outer walls of the vasculature of the anastomosis.

In one embodiment, the method may further include the first end being tapered away from the medial region such that a diameter of the first end at a distal end from the medial region is larger than a diameter of the first end at a proximal end of the medial region.

In one embodiment, the method may further include step (f) further comprising locating at least one of the maximum principal strain, maximum principal stress, or deformation of the vessel to at least 5 mm from a suture line of the vascular anastomosis.

In one aspect of the present disclosure, a method of treating a vascular anastomosis is disclosed comprising the steps of: (a) coupling a first vessel and a second vessel to construct a vascular anastomosis; (b) providing a perivascular wrap; (c) contacting the perivascular wrap to the vascular anastomosis after the construction of the anastomosis; (d) molding the perivascular wrap from a first shape to a second shape wherein the second shape conforms to the geometry of the vascular anastomosis such that the perivascular wrap provides artery-mimetic support to the vascular anastomosis in the range of 0.1-2.0 MPa.

In one embodiment, the method may further include wherein the vasculature comprises a vein and an artery.

In one embodiment, the method may further include wherein the vasculature comprises a graft.

In one embodiment, the method may further include the shape memory polymer comprises poly (ε-caprolactone).

In one embodiment, the method may further include the shape memory polymer comprises poly (ε-caprolactone)-co-(α-allyl carboxylate ε-caprolactone).

In one embodiment, the method may further include the molding of the perivascular wrap is formed to have direct contact with the outer walls of the vasculature of the anastomosis.

In one embodiment, the method may further include the first end being tapered away from the medial region such that a diameter of the first end at a distal end from the medial region is larger than a diameter of the first end at a proximal end of the medial region.

In one embodiment, the method may further include step (f) further comprising locating at least one of the maximum principal strain, maximum principal stress, or deformation of the vessel to at least 5 mm from a suture line of the vascular anastomosis.

DETAILED DESCRIPTION

Figure 1:
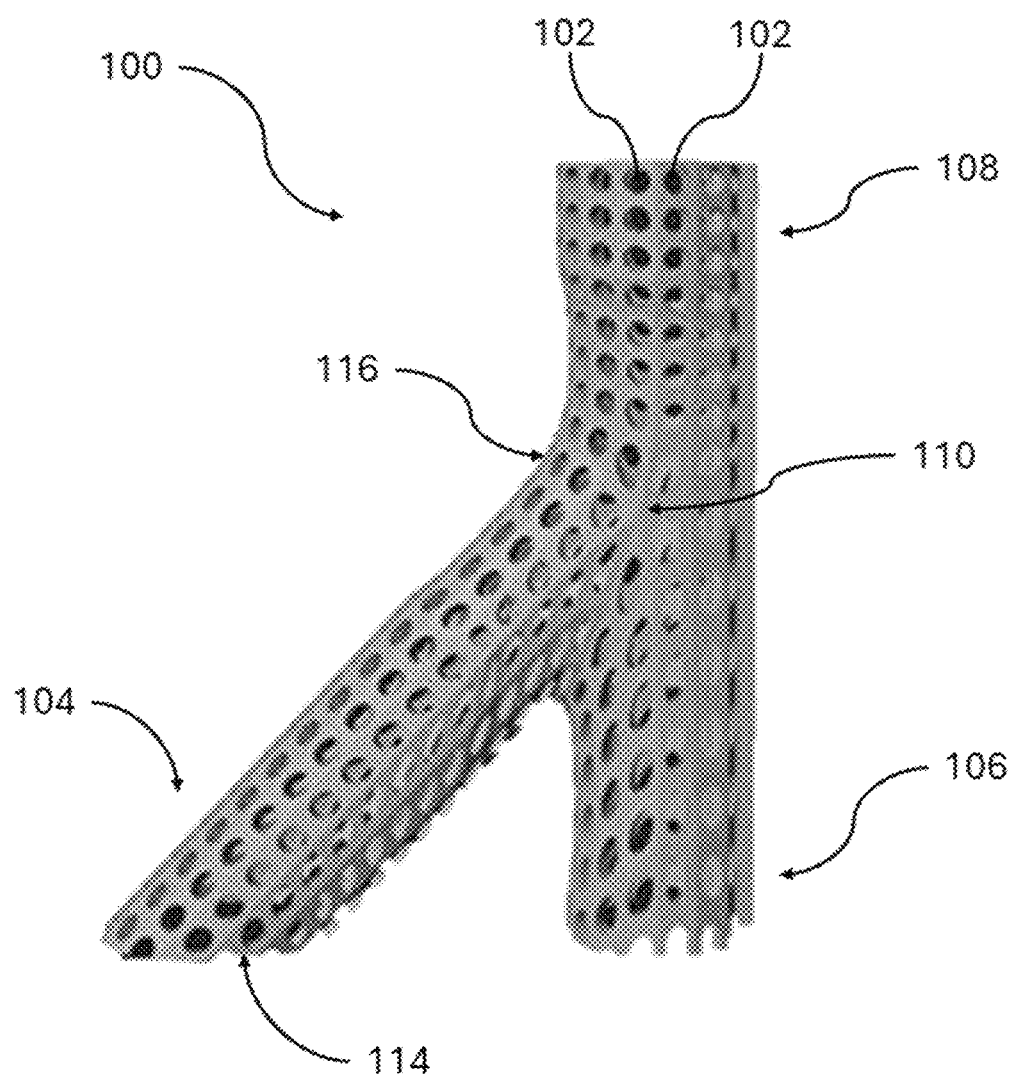
FIG. 1 is a depiction of a perivascular wrap.

Various embodiments of the present disclosure relate to devices and methods for treating arteriovenous fistulas (AVFs) and/or arteriovenous grafts (AVGs) as well as other vascular conditions. There are currently no approaches on the US market to treat AVFs and/or AVGs in a way that results in much better clinical outcomes for patients, that reduces neointimal hyperplasia, that supports the vasculature at a surgical site to induce outward remodeling and not inward remodeling of the vessel, and that reduces overall vein wall tension and radial stress as a result of increased blood pressure and flow. Further, there are no clinical approaches that improve dialysis access site maturation rates and prevents patency failures. Current devices, such as those listed under product code PFV, treat AVFs and AVGs that have already had patency failures. Systemic therapeutics to improve hemodialysis or vein graft patency have so far exhibited little to marginal benefit, motivating device or combination approaches localized to the vein, especially near the venous anastomosis where the majority of stenotic lesions typically develop. Perviascular approaches to improve vascular outcome, maturation, and patency of AVFs, AVGs, and vein bypass grafts for peripheral and coronary bypass surgeries have, to date, focused primarily on either attenuating vein wall tension and stresses with mechanical support or promoting processes that are involved in outward remodeling (e.g., adventitial angiogenesis or elastin fragmentation), but not both at the same time.

The device and methods disclosed herein are uniquely suited to accomplish both of these objectives—mechanical support and neovascularization—to improve maturation and patency of AVFs and AVGs. Various embodiments as disclosed herein can help alleviate neointimal hyperplasia by reducing vein wall tension and compliance mismatches that lead to neointimal hyperplasia and stenosis, reducing the occurrence of low, oscillating wall shear stresses as well as very high wall shear stresses that can lead to neointimal hyperplasia and eventually failure of the vascular anastomosis. Further, the perivascular wraps and methods of use as disclosed herein can promote an outward shift, rather than an inward shift, of vascular smooth muscle cells and myofibroblasts to reduce neointimal hyperplasia. Additionally, the perivascular wraps and methods of use as disclosed herein can provide a custom fit of the device to a patient's AVF/AVG geometry to provide greater vessel wall surface area coverage, mechanical support, and more uniform outward remodeling.

A blood vessel is generally made of three distinct layers surrounding the lumen through which blood flows. The term "lumen," as used herein, may refer to a cavity of a tubular organ such as a blood vessel, graft, vein, artery, and the like, whether natural or synthetic. The layers surrounding the lumen include the outermost adventitia, the media, and the intima. The cells of the intima may be supported by the internal elastic membrane that separates the intima from the media.

The intima is generally made up of a single layer of endothelial cells which may be in direct contact with blood flow and would generally surround the lumenal area. The term "neointimal hyperplasia," as used herein, may refer to post-intervention, pathological, vascular remodeling of a vessel due to the proliferation and migration of vascular smooth muscle cells from the media into the intima layer, resulting in vascular wall thickening, decrease in lumenal area, and the gradual loss of lumenal patency. Due to neointimal hyperplasia, the neointima may obstruct blood flow through the access site and may require additional interventions to be employed to combat the formation of the neointima so as to save the access site. If the additional interventions are not successful, the deposit of the neointima may force abandonment of the access site. In addition to the issues of neointimal hyperplasia, arteries and veins have different mechanical properties-arteries are stiffer and thicker than veins and are far better equipped to withstand the high pressures and flow rates of the arterial environment. The difference in mechanical properties between arteries and veins may lead to compliance mismatch at a vascular anastomosis and may expose the vein to an order of magnitude increase in pressure and flow. This exposure may lead to heightened vein wall tension and radial stresses, flow turbulence, and stenotic wall shear stresses (WSSs) (low, oscillating as well as high WSSs). The net effect is that in AVFs and AVGs, the exposed vein maladapts to the new vasculature environment by thickening its walls inwardly via neointimal hyperplasia, causing stenosis and obstructing blood flow through the access site that results in failures of both maturation and patency and ultimately failure of the AVF/AVG.

To address the issues of AVF/AVG failure, embodiments of the present invention include a perivascular wrap that may be deployed around a vascular anastomosis during surgery. As shown in FIG. 1, a perivascular wrap 100 may include a custom-fittable external support. In some embodiments, the perivascular wrap 100 may include a shape memory polymer which is specifically engineered to enhance patency and longevity of AVFs and AVGs, as well as the degree and speed of AVF maturation via reduction of neointimal hyperplasia, stenosis, modulation of wall tension and stresses, and promotion of outward vein remodeling.

Figure 2A:
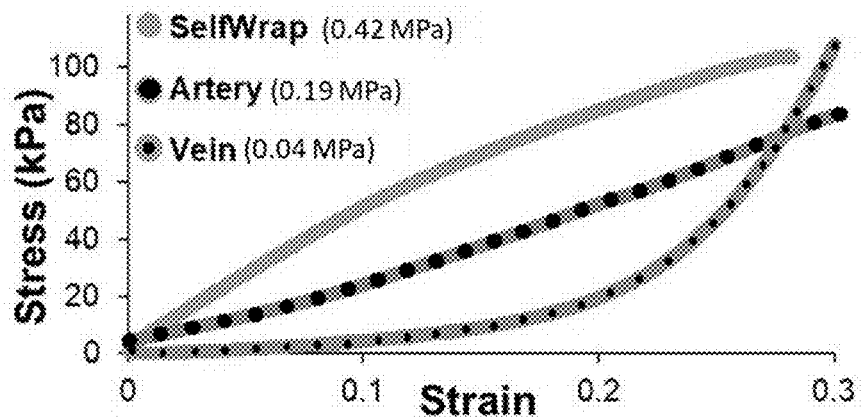
FIGS. 2A and 2B are graphical representations of the Young's Modulus and artery-mimetic stiffness of a perivascular wrap of the instant disclosure.
Figure 2B:
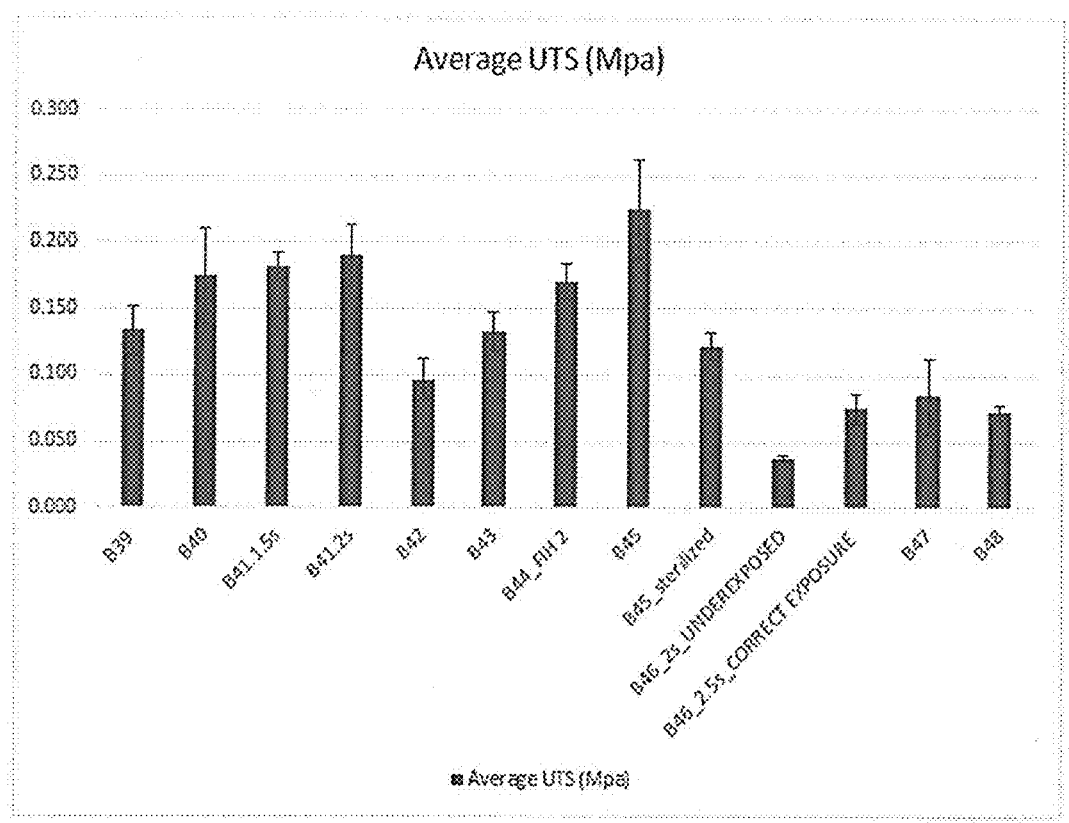

In certain embodiments of the present disclosure, the perivascular wrap may include artery-mimetic mechanical support to the vascular anastomosis. As shown in FIGS. 2A and 2B, the artery-mimetic mechanical support may range from 0.1 to 2.0 MPa, from 0.2 to 2.0 MPa, from 0.2 to 1.8 MPa, from 0.2 to 1.6 MPa, from 0.4 to 1.6 MPa, from 0.5 to 1.5 MPa, from 0.6 to 1.4 MPa, from 0.7 to 1.3 MPa, from 0.8 to 1.2 MPa, or from 0.9 to 1.1 MPa in some embodiments. By providing artery-mimetic mechanical support, the perivascular wrap may help the vasculature to adapt to changes in pressure, such as a vein adapting to the increased pressure from the artery, while also obviating compliance mismatch issues between the mechanical properties of the different vascular connections used in the surgery. The term "vascular connections" as used herein may be understood to include vein to artery connections, artery to vein connections, vein to graft connections, artery to graft connections, graft to vein connections, and graft to artery connections. The vein, artery, and/or grant may be natural or synthetic. More than one connection may be utilized in various embodiments. It will also be understood that the term "vessel" as used herein may include a vein, artery, or graft, synthetic or natural.

Referring back to FIG. 1, in certain embodiments the perivascular wrap may include macropores 102 that helps to promote outward remodeling, which is needed for successful maturation. The successful maturation process may be promoted by neovascularization, or new microvessel formation, on the outer adventitial layer of the vein. This may shift the migration of vascular smooth muscle cells and myofibroblasts outward rather than inward to mitigate neointimal hyperplasia and mitigate hypoxic conditions within vein walls that cause neointimal hyperplasia.

In some embodiments, the perivascular wrap may be slowly biodegradable which helps to ensure full mechanical support throughout the critical vein remodeling period while also being fully resorbed within approximately 6 months (FIG. 3) to minimize infection risk, compliance mismatching, and other complications such as skin erosion associated with permanent implants. It will be understood that the critical vein remodeling period may be from the completion of the surgery until 2 months, 3 months, 4 months, 5 months, or 6 months post-surgery. In some embodiments, the perivascular wrap may be at least 1%, 10%, 20%, 30%, 40%, 50%, 60%, or 70% degraded at 3 months post-surgery. In certain embodiments, the perivascular wrap may be at least 20% to 50% degraded at 3 months post-surgery.

In some embodiments of the present disclosure, the perivascular wrap may include a shape memory polymer. Shape memory polymer materials may melt below body temperature, transitioning from an elastic to viscoelastic state. The transition may allow the wrap to be moldable to a patient's specific anastomosis geometry which may enhance vein wall surface area coverage to better dissipate the heightened wall tensions and stresses in the vascular anastomosis environment. The enhanced vein wall surface area coverage and limited spacing between wrap and vein wall may also mitigate asymmetric wall thickening that can cause turbulent, irregular flow and subsequent neointimal hyperplasia, especially around anastomoses.

In certain embodiments, a shape memory polymer may include a class of poly (ε-caprolactone) ("PCL")—based SMPs, PCL-co-(α-allyl carboxylate ε-caprolactone) (x % PCL-y % ACPCL) [where x % and y % are molar percentages]. Previously investigated polymers and shape memory alloys demonstrated promising anti-intimal hyperplasia effects in vein grafts in various CABG and PVBG preclinical models, but are difficult to apply to the variable, geometrically-complex anastomoses encountered clinically, and as described herein.

Thermo-responsive shape memory polymers address this issue. In some embodiments, shape memory polymers may include an initial, "original" or "permanent" shape, and then transition to a different, "temporary" shape by heating above a shape transition temperature (T) (e.g., melting Temp. "Tm"). Heating shape memory polymers above their T, during hemodialysis access surgery enables facile molding of the perivascular wraps around geometrically-complex anastomoses without sutures or large incisions, thereby reducing surgery times and associated infection risks while completely obviating the risk of suture dehiscence.

The term "implanted shape" as used herein will be understood to include a shape that has been given to a material by exerting a force on the material and/or exposing the material to certain temperatures (i.e., programming step). While the material can retain its temporary shape for any length of time, the shape is referred to as being temporary because the shape exists only when external forces exerted on the material. Furthermore, in some embodiments the materials can lose their temporary shape when exposed to a temperature above a melting temperature of the material.

The term "original shape" as used herein will be understood to include a shape of the material when the polymers of the material are in their native, pre-implanted state. Once a material is in its original shape, a material will generally retain the original shape unless an external force or the like is applied to the material. Some embodiments of materials revert to and/or retain an original shape when exposed in a physically unstressed state to a temperature above a melting temperature of the material (i.e., recovery step). Crosslinks between the plurality of polymers that comprise the materials, either chemical or physical in nature, help prevent irreversible, plastic deformation during programming and recovery steps.

In one embodiment of the present disclosure, the perivascular wrap may be in the form of a biodegradable polymeric scaffold that surrounds a vascular anastomosis, the polymeric scaffold including a shape memory polymer including a first monomer that is crosslinkable and a second monomer that not crosslinkable. In some embodiments, the biodegradable polymeric scaffold may include a shape memory polymer comprising at least one crosslinked polymer. The perivascular wrap may be capable of transforming between an original, permanent shape and an implanted, temporary shape; and wherein the device is mechanically compliant at from about 20° to about 50° C.

In embodiments of the aforementioned aspects of the disclosure, the first monomer may be allyl functionalized and may include an allyl carboxylate group. Additionally, the first monomer, the second monomer, or both may be an ester. In other embodiments, the first monomer, the second monomer, or both include ε-caprolactone (CL). Additionally, the plurality of crosslinked polymers may include a poly (ε-caprolactone)-co-α-allyl carboxylate ε-caprolactone) polymer. In other embodiments, the plurality of crosslinked polymers may include about 1 mol % to about 30 mol % of the first monomer. In other embodiments, the plurality of crosslinked polymers includes a shape transition temperature from about 20° C. to about 50° C.

In some embodiments the compound may be comprised of about 1 mol %, 5 mol %, 10 mol %, 15 mol %, 20 mol %, 25 mol %, 30 mol %, 35 mol %, 40 mol %, 45 mol %, or 50 mol % of the first monomer. In other embodiments the compound is comprised of about 1 mol % to about 50 mol % of the first monomer, about 1 mol % to about 30 mol % of the first monomer, or about 1 mol % to about 15 mol % of the first monomer. In such embodiments the remainder of the polymer can be comprised of the second monomer.

In addition to PCL-ACPCL, some embodiments may further contain additional components. In one embodiment, PEGDA (poly (ethylene glycol) diacrylate) may also be a component of the shape memory polymer.

As indicated above, embodiments of the present disclosure are capable of surrounding a vascular anastomosis. In certain embodiments, the vascular anastomosis may include a vein, artery, or graft, and may be natural or synthetic.

Once implanted, embodiments of the present disclosure may form a seamless and sutureless sheath. The sheath may be a mesh or netting and may be macroporous. Additionally, once implanted, some embodiments of the disclosure may have resilient radial expression in a manner that mimics the compliance properties of vessels. The perivascular wraps may be deformable by at least one of stretching or bending along its length to conform to the shape of the tissue.

Embodiments of the present disclosure may afford the unique capability to provide a custom fit for each anastomosis. This spatial control between the various vessels critically affects adventitial microvessel formation and outward remodeling that can mitigate neointimal formation. It can also help to minimize asymmetric wall thickening that causes turbulent irregular flow and subsequent thrombosis and hyperplasia, especially around anastomoses.

Figure 4:
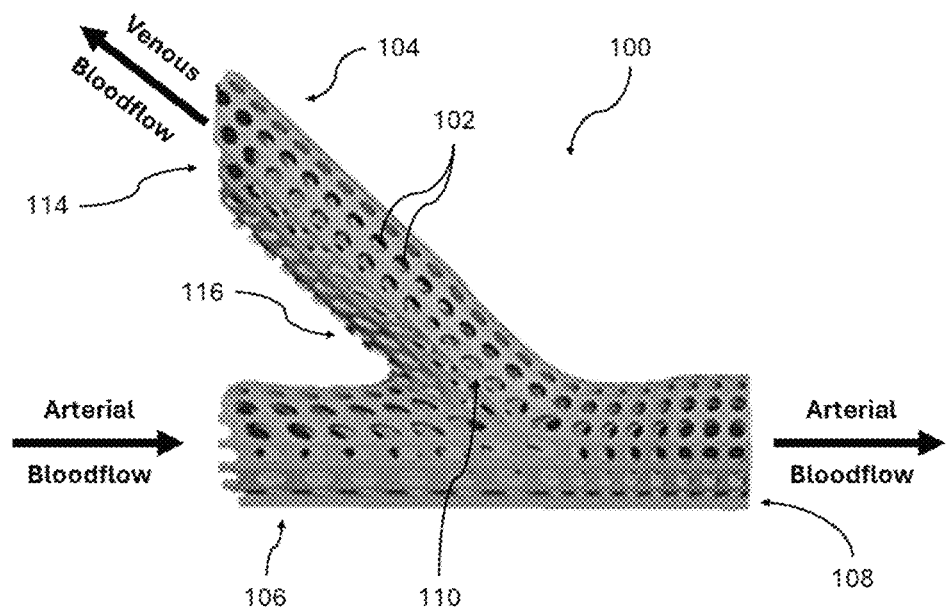
FIG. 4 is a picture of an embodiment of a perivascular wrap in an implanted state and an un-implanted state.
Figure 5:
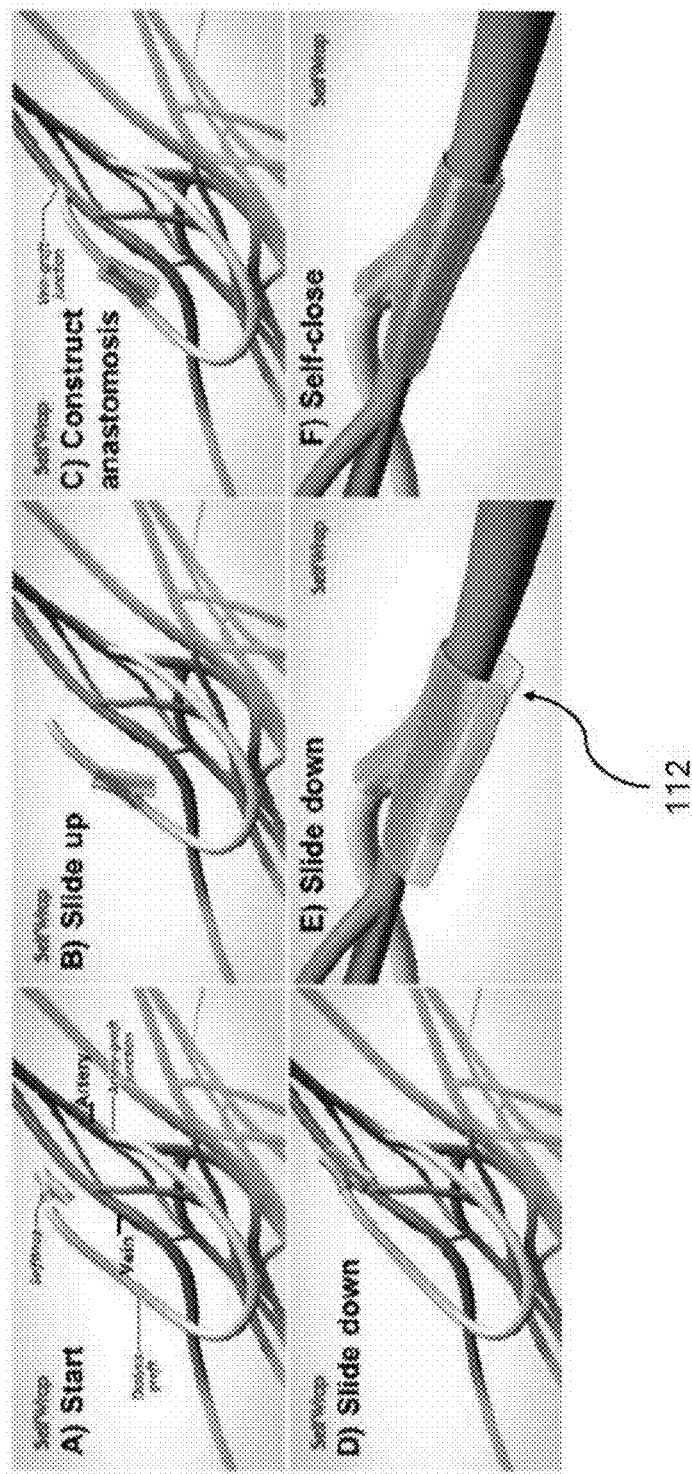
FIG. 5 is an illustrative implantation procedure of an embodiment of the instant disclosure.

In certain embodiments of the present disclosure, a method of treatment for a vascular anastomosis is disclosed. Generally, a perivascular wrap may be implanted during a vascular access creating surgery in which a vessel-vessel connection is created in a patient's arm in the form of a fistula or graft. Users will consist of surgeons that perform vascular access creation surgeries, which include vascular surgeons, transplant surgeons, and general surgeons depending on geographical location. In some embodiments, the perivascular wrap may Referring to FIGS. 4 and 5, in some embodiments, the perivascular wrap may be disposed about a transected vessel wherein a vessel is dissected out with the aim of creating a vascular fistula. In some embodiments, the fistula may be created at an acute angle of 60 degrees or less, 50 degrees or less, 45 degrees or less, 40 degrees or less, 35 degrees or less, 30 degrees or less, 25 degrees or less, or 20 degrees or less. Prior to suturing the dissected vessel to the target vessel, a user may hydrolytically dilate the dissected vessel.

In some embodiments, the perivascular wrap may have a first end 104, a second end 106, a third end 108, and a medial region 110. The first end 104 may provide for insertion of the transected vessel and be disposed around the transected vessel once the anastomosis surgery is complete. The second end 106 and third end 108 may provide for openings in which the target vessel travels through a portion of the perivascular wrap. In some embodiments, the blood flow may be in a direction such that the blood flow in the vessel enters the second end 106 and exits the third end 108. In some embodiments, the transected vessel may be a vein. In some embodiments, the target vessel may be an artery. In other embodiments, the transected vessel may be a graft or an artery. In certain embodiments, the target vessel may be a vein or graft. The medial region 110 may be disposed about a medial position of the perivascular wrap and envelop the junction of the vasculature.

In some embodiments, selection of the sizing of a perivascular wrap may be required so that the inner diameters of the wrap properly fit around the anastomosis and vessels without causing too much constriction of the vessels, while at the same time not being too loose and failing to provide adequate support. If the device chosen is oversized compared to the diameters of the vessels, the perivascular wrap may not have any impact on maturation or patency. If the device chosen is undersized compared to the diameters of the vessels, maturation of the anastomosis may be impeded due to constriction of normal vessel dilation.

The determination of the outer and inner diameters of the vessels may be done by any known techniques in the art. In some embodiments, the determination of the outer diameter of a vessel may be done by looking at the vessel directly and estimating the approximate size. In other embodiments, the vessel may be directly measured with a measuring device such as a measuring tape or caliper. In other embodiments, the outer diameter may be measured via ultrasound. Doppler ultrasound machines are known in the art and include examples such as Phillips HD9 Ultrasound System and MSL MSLCU08. In addition to determining the outer diameter of a vessel, ultrasound techniques can also be useful in determining the inner diameter of a vessel. This can be useful in determining whether a vessel has any occlusions or stenosis of the vessel prior to beginning the surgery.

Once the outer and/or inner diameter of the vessels of interest have been determined, an appropriately sized perivascular wrap may be selected. As provided previously, the selection of the wrap should be made so that it contacts the vessels without causing too much constriction of the vessels, while at the same time not being too loose and failing to provide adequate support. To produce optimal results as provided previously in this disclosure, a constriction of from 0% to 30% of the vessel should be achieved. In some embodiments, the constriction may be from 5% to 25%, 10% to 20%, and about 15%. In some embodiments, the constriction may be from 15% to 30%. In other embodiments, the constriction may be from 20% to 30%. And yet in still other embodiments, the constriction may be from 15% to 20%. The determination of constriction is known in the art. The authors of this disclosure determined constriction based on the methods disclosed in Franz, T. (2010) Tailored Sizes of Constrictive External Vein Meshes for Coronary Artery Bypass Surgery. *Biomaterials.* 31 (2010) 9301-9309.

In certain embodiments, it will be understood that in determining the constriction and appropriate perivascular wrap sizing, a certain percentage of dilation may occur post operatively. One may expect up to 30% dilation to occur post-operatively and therefore must account for that percentage increase to the outer diameter of the vessels after the determination of the outer diameter has been conducted. In some embodiments, the dilation percentage may range from 15%-30%, from 20%-30%, or from 25%-30%. In other embodiments, the dilation percentage may range from 10%-30%, from 5%-30%, or from 0%-30%.

In one embodiment, as an example, the perivascular wrap may be provided in 4 sizes as displayed in Table 1 below.

TABLE 1

Device Selection

| Pre-Operative (Baseline) Ultrasound Vein OD (mm) | Device Selection |
|---|---|
| OD < 2.4 mm | Device A |
| 2.4 mm ≤ OD < 3.1 mm | Device B |
| 3.1 mm ≤ OD < 4.4 mm | Device C |
| OD ≥ 4.4 mm | Device D |

Each perivascular wrap had an internal diameter that was sized to correspond to a range of vessel diameters so that the wrap would be made so that it contacts the vessels without causing too much constriction of the vessels, while at the same time not being too loose and failing to provide adequate support. Generally, if the outer diameter of the vessels were 2.4 mm, then device A would be selected. If the outer diameter was from 2.4 mm to 3.1 mm, then device B would be selected. If the outer diameter was from 3.1 mm to 4.4 mm, then device C would be selected. And if the outer diameter was greater than 4.4 mm, then device D would be selected. Within these selections as exemplified, a minimum and maximum diameter may be considered so that the minimum size and maximum size of a usable vessel is selected.

It will be understood that the above example is merely an illustration and that one of skill in the art will appreciate that the sizing of the various devices may be altered. Generally, it will be understood that with embodiments like those being currently described, a one-size-fits-all is difficult to make fit the various sizes of vessels of a patient, and between patients. Other embodiments described below may address a one-size-fits-all approach.

Once the appropriate sizing of the perivascular wrap has been selected, it may be placed on the transected vessel by passing the transected vessel through the first end 104 and sliding the wrap up the vessel. Then, the vascular anastomosis may be constructed. In some embodiments, the target angle of the anastomosis may be about 30 degrees, may be 25-35 degrees, or may be 25-40 degrees. In some embodiments, the desired angle is less than 45 degrees. Once the anastomosis is constructed, the perivascular wrap may be slid down the previously-transected vessel and the medial region 110 of the wrap may be positioned around the anastomosis. The target vessel may be positioned in the wrap where the target vessel may travel from the second end 106 to the third end 108. The perivascular wrap should be positioned such that the open flap portion 112 is closed on itself and the wrap envelops the anastomosis. In some embodiments, the perivascular wrap may be molded to the specific geometry of the vascular anastomosis so as to provide optimal and maximal support. In some embodiments, portions of the wrap may be molded and pressed against each other to "stick" the wrap to itself and create a sutureless sheath around the anastomosis. In some embodiments, the wrap may need to be pressed together for at least 5 seconds to provide adequate force to stick the wrap to itself. Once the wrap is enveloping the anastomosis, the access opening may be closed.

In some embodiments, patency of the vascular anastomosis after surgery may be determined through the thrill as well as through ultrasound measurements.

Figure 6A:
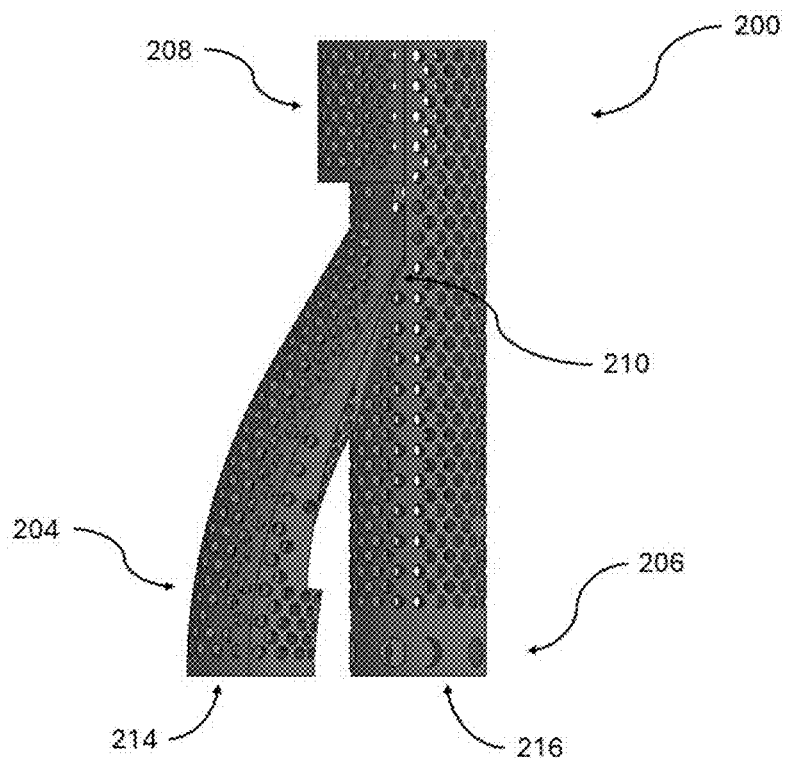
FIG. 6A is a depiction of an embodiment of the butterfly design.
Figure 6B:
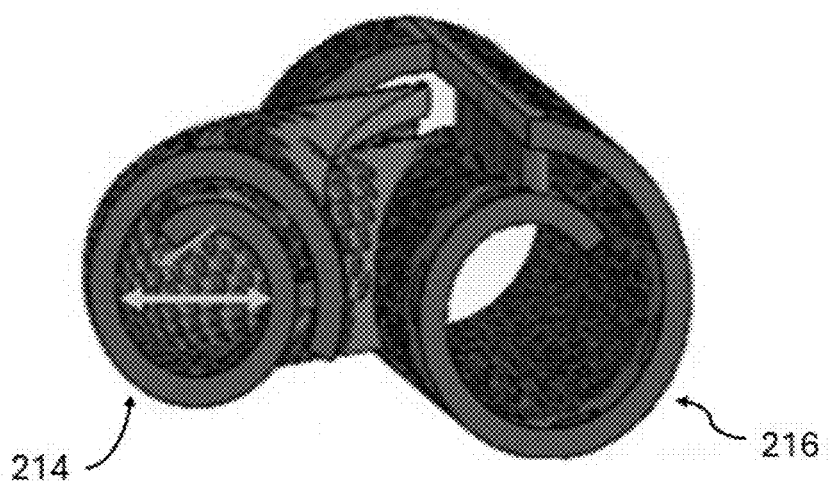
FIG. 6B is a axial view of the butterfly design of FIG. 6A that depicts the overlapping flaps which can be unfurled to open both passageways for positioning onto an anastomosis.

In other embodiments, a one-size-fits-all approach may be taken wherein the perivascular wrap may use a "butterfly" design such that the wrap is able to fully open from its original shape, be placed around the constructed anastomosis, and then be molded and sealed to itself to create a sutureless sheath. As shown in FIGS. 6A and 6B, the "butterfly design" may include a perivascular wrap 200 which includes a similar first end 204, second end 206, third end 208, and medial region 210 as previously disclosed. In comparison, the butterfly perivascular wrap may fold open at both passageways 214, 216. As shown in FIG. 6B, one can see the overlapping flaps which unfold to open both passageways of the device. The method of use of the butterfly perivascular wrap may include transecting a vessel wherein a vessel is dissected out with the aim of creating a vascular fistula. In some embodiments, the fistula may be created at an acute angle of 60 degrees or less, 50 degrees or less, 45 degrees or less, 40 degrees or less, 35 degrees or less, 30 degrees or less, 25 degrees or less, or 20 degrees or less. Prior to suturing the dissected vessel to the target vessel, a user may hydrolytically dilate the dissected vessel.

In some embodiments, the transected vessel may be a vein. In some embodiments, the target vessel may be an artery. In other embodiments, the transected vessel may be a graft or an artery. In certain embodiments, the target vessel may be a vein or graft. The medial region 110 may be disposed about a medial position of the perivascular wrap and envelop the junction of the vasculature.

The transected vessel and target vessel are joined to construct the vascular anastomosis, and once the anastomosis is complete, the butterfly perivascular wrap may be positioned around the anastomosis with the previously-transected vessel positioned at the first end 204 and traveling along the first passageway 214. The target vessel may be positioned along the second passageway 216 and enter the passageway and exit the passageway at the second end 206 and third end 208. The medial regions 210 may be positioned about the junction of the vessels joined together.

Figure 7:
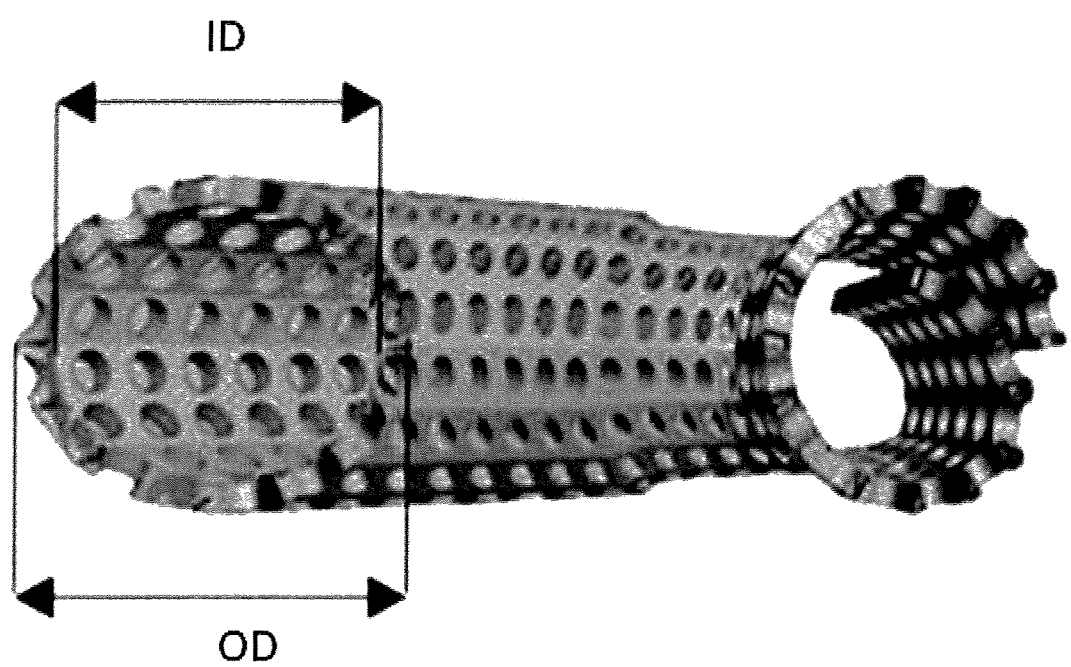
FIG. 7 is an illustration of the inner diameter and outer diameter of a passageway of a perivascular wrap.

In some embodiments of the present disclosure, the perivascular wrap may include a tapered first end away from the medial region. As show in FIG. 4, the first end 104 may include a distal end 114 that is distal to the medial region 110 and a proximal end 116 that is proximal to the medial region. As depicted in FIG. 7, the perivascular wrap of the disclosed embodiments may include an inner diameter (ID) and an outer diameter (OD). These diameters may taper from the proximal end to the distal end such that the ID and OD at the distal end is larger than the proximal end. It will be understood that both the perivascular wrap and butterfly design may include a tapered end. Further, it will be understood that while only the first end of the wrap is depicted as being tapered, the second end and/or third end may also be tapered in the same fashion away from the anastomosis.

Figure 8:
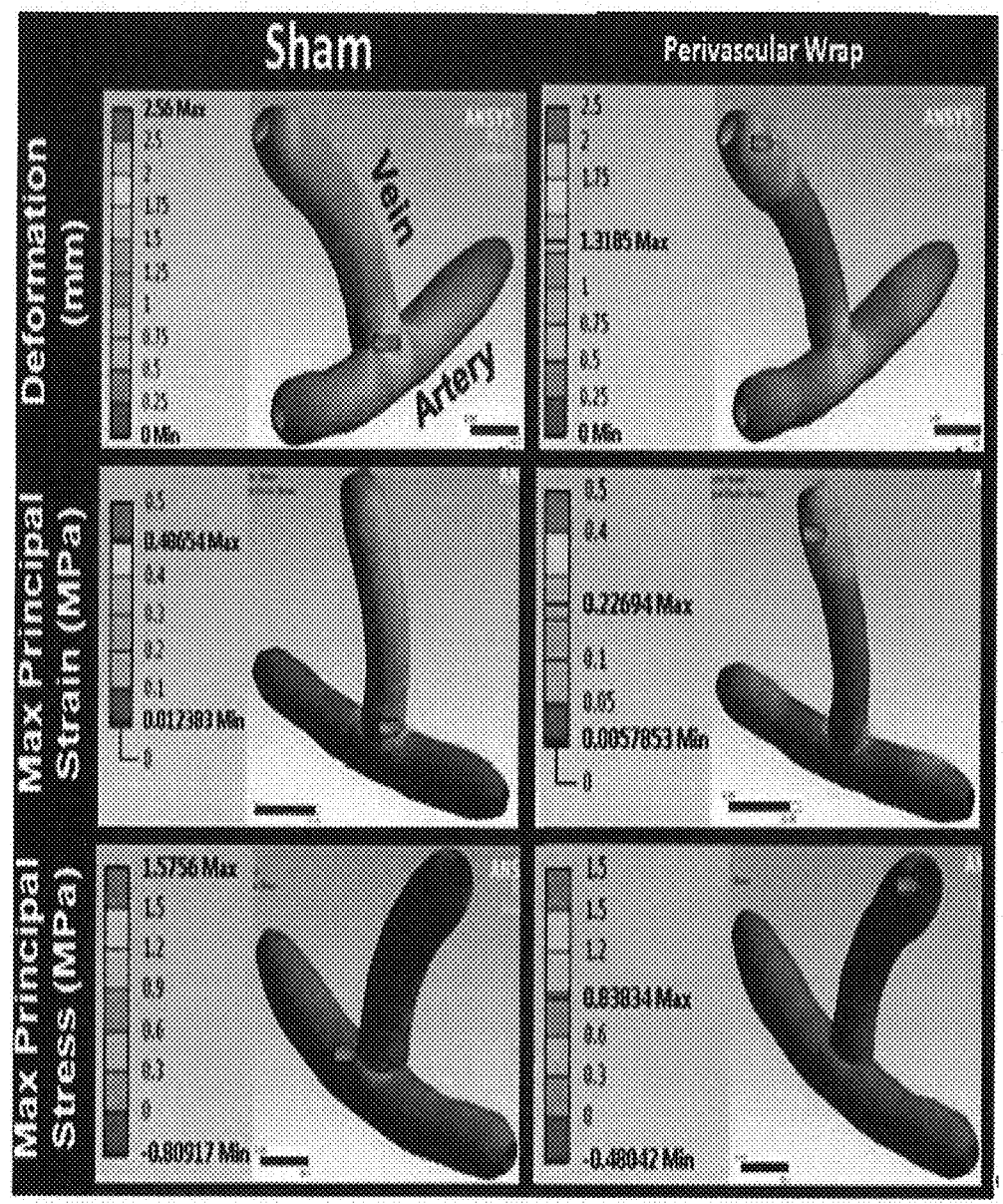
FIG. 8 is a FSI CFD simulation.

Computational fluid dynamic modeling indicate that the perivascular wraps of the present disclosure provide biomechanical and hemodynamic benefits when applied. Through a series of ex vivo experiments and follow-up CFD simulations incorporating the AVF geometry from MRI images, inlet boundary conditions corresponding to empirical parameters resulted in high-fidelity matching between 4D Flow MRI results and CFD-generated velocity profiles. When a perivascular wrap as disclosed herein is applied to a vascular anastomosis, vessel wall deformation, maximum principal elastic strain, and maximum principal stress were reduced (FIG. 8). It will be understood by those skilled in the art that principal stress approximates circumferential wall stress (CWS) in a pressurized cylinder. When a vein is transferred from its native hemodynamic environment to that of the arterial circulation, the CWS can be increased more than 100×, leading to neointimal hyperplasia development. Therefore, by reducing CWS via external wrapping of vessel, reductions in neointimal hyperplasia can occur. The perivascular wraps of the instant disclosure not only reduce the strain and CWS, but also reduces compliance mismatches, a significant factor in the development of neointimal hyperplasia, and shift maximum strain, stress, and deformation locations away from the junction of the vascular anastomosis. The unique thermomechanical properties, and anatomic fit of the perivascular wrap to vascular anastomoses eases compliance mismatching between vessels, especially those of veins and arteries, and mitigate some of these causes of neointimal hyperplasia. As demonstrated in FIG. 8, the movement of the maximum stress, strain, and deformation away from the vascular anastomosis to the distal ends of the wrap are shown by the arrows. In some embodiments, each of the maximum strain, stress, and deformation may be moved away from the suture line of the junction by 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, or 40 mm. It will be understood that the movement of the strain, stress, or deformation, away from the suture line may not be equal among the three. In one embodiment, at least one of the categories of max strain, stress, or deformation, is moved at least 3 mm, at least 5 mm, at least 7 mm, at least 10 mm, at least 15 mmm, at least 20 mm, at least 30 mm. In one embodiment, at least two of the categories of max strain, stress, or deformation, is moved at least 3 mm, at least 5 mm, at least 7 mm, at least 10 mm, at least 15 mmm, at least 20 mm, at least 30 mm. In one embodiment, all three of the categories of max strain, stress, and deformation, are moved at least 3 mm, at least 5 mm, at least 7 mm, at least 10 mm, at least 15 mmm, at least 20 mm, at least 30 mm.

In some embodiments, the perivascular wraps as disclosed herein disclose significant neovascularization over controls. STRATAFIX® (degradable control comprised of PGA-PCL), and standard negative plastic (nondegradable control comprised of high density polypropylene, HDPE) were implanted in the paravertebral muscle tissue of four New Zealand White rabbits, with four implant sites per animal, for a period of two weeks. A perivascular wrap as disclosed herein, and STRATAFIX® were made into 1 mm×1 mm×10 mm strips and ethylene oxide sterilized, while the nondegradable HDPE control was 1 mm×10 mm strips sterilized via autoclave. A piece of sterile non-absorbable suture was placed in the area of each implantation site as a marker for absorption. After 2 weeks, implantation sites were grossly observed, then collected and processed for histological evaluation. No gross evidence of bioreactivity was observed at any implant site, and axillary lymph nodes of each animal appeared normal grossly. Histological scoring of inflammation (Table 2) and heating response (Table 3) were conducted for each implantation site.

TABLE 2

Histological scoring of inflammatory cells and necrosis to derive inflammation score.

| Cell Type/ Response | Score | | | | |
|---|---|---|---|---|---|
| | 0 | 1 | 2 | 3 | 4 |
| Polymorpho-nuclear Cells | 0 | Rare, 1-5/phf[a] | 5-10/phf | Heavy Infiltrate | Packed |
| Lymphocytes | 0 | Rare, 1-5/phf | 5-10/phf | Heavy Infiltrate | Packed |
| Plasma Cells | 0 | Rare, 1-5/phf | 5-10/phf | Heavy Infiltrate | Packed |
| Macrophages | 0 | Rare, 1-5/phf | 5-10/phf | Heavy Infiltrate | Packed |
| Giant Cells | 0 | Rare, 1-2/phf | 3-5/phf | Heavy Infiltrate | Sheets |
| Necrosis | 0 | Minimal | Mild | Moderate | Severe | phf[a] = per high powered (400×) field.

TABLE 3

Histological scoring of neovascularization, fibrosis, and fatty infiltrate

| Cell Type/Response | Score | | | | |
|---|---|---|---|---|---|
| | 0 | 1 | 2 | 3 | 4 |
| Neovascularization | 0 | Minimal capillary, proliferation, focal. 1-3 buds | Groups of 4-7 capillaries with supporting fibroblastic structures | Broad band of capillaries with supporting structures | Extensive band of capillaries with supporting fibroblastic structures |
| Fibrosis | 0 | Narrow band | Moderately thick band | Thick band | Extensive band |
| Fatty Infiltrate | 0 | Minimal amount of fat associated with fibrosis | Several layers of fat and fibrosis | Elongated and broad accumulation of fat cells about the implant site | Extensive fat completely surrounding the implant |

The results of the histological analysis indicate that the perivascular wrap demonstrates no reaction at two weeks compared to the STRATAFIX® PGA-PCL degradable control (Bioreactivity Rating of 0.6) nor to the standard negative HDPE plastic (Bioreactivity Rating of 1.7). Any Bioreactivity Rating <3.0 is considered nonreactive. The perivascular wrap implantation sites were characterized by poorly defined effacement with moderate accumulations of macrophages and lymphocytes with numerous vascular aggregates and supporting connective tissue structures. Ingrowth of plump, spindle-shaped cells consistent with activated fibroblasts were present in most perivascular wrap implantation sites. STRATAFIX® sites were characterized by well-demarcated effacement by macrophages with smaller numbers of granulocytes and lymphocytes, and aggregates of capillaries observed in certain regions. Nondegradable HDPE sites were characterized by effacement with macrophages, granulocytes, and lymphocytes and incomplete bands of thin fibrous tissue. The assessment of residual test article after two weeks indicated moderate, multi-focal presence of perivascular wrap remaining, with a score of 3.8. Based on the criteria of the protocol, the perivascular wraps of the instant disclosure are considered non-reactive and meets the requirements of ISO 10993-6 guidelines.

Figure 9:
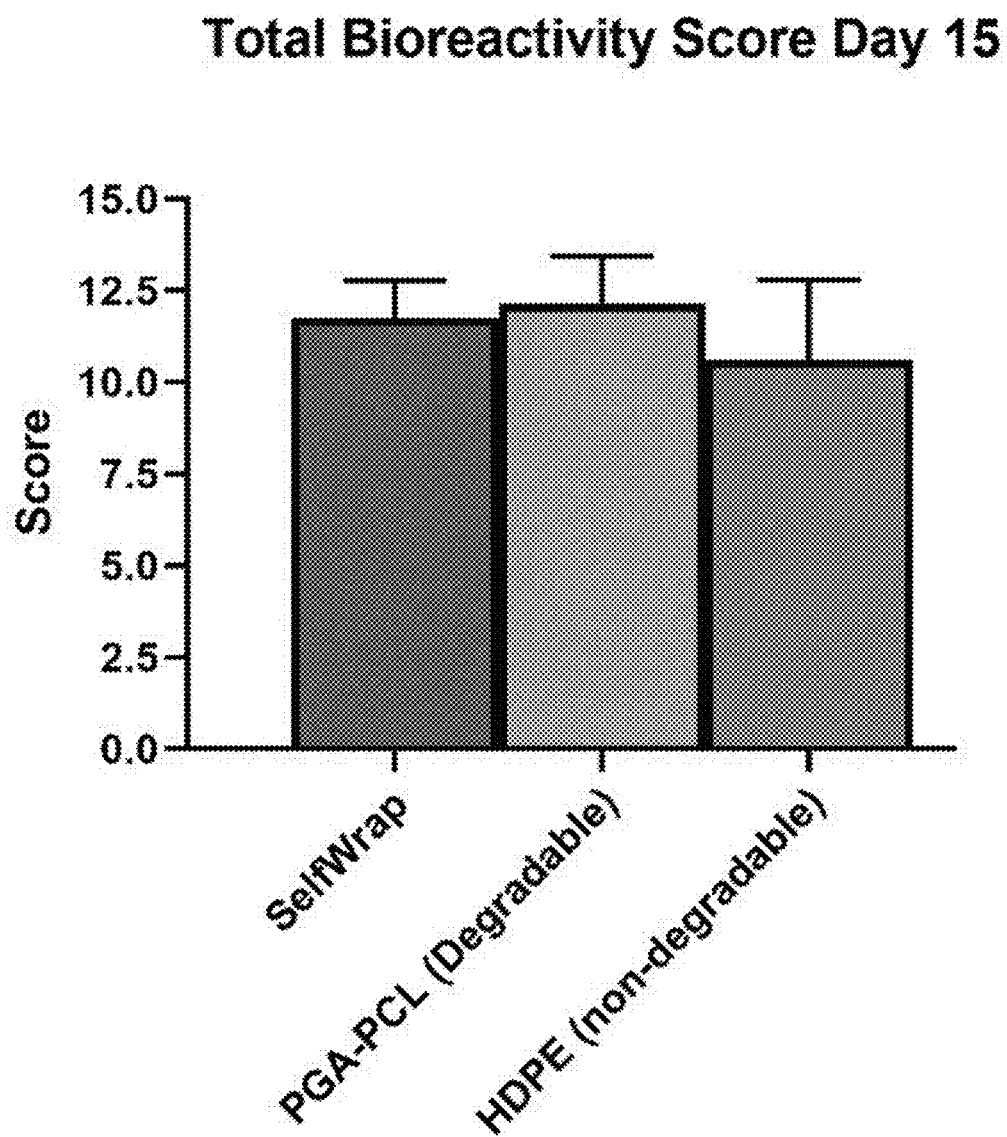
FIG. 9 is a graphical representation of data for bioreactivity at 15 days post-surgery.
Figure 10:
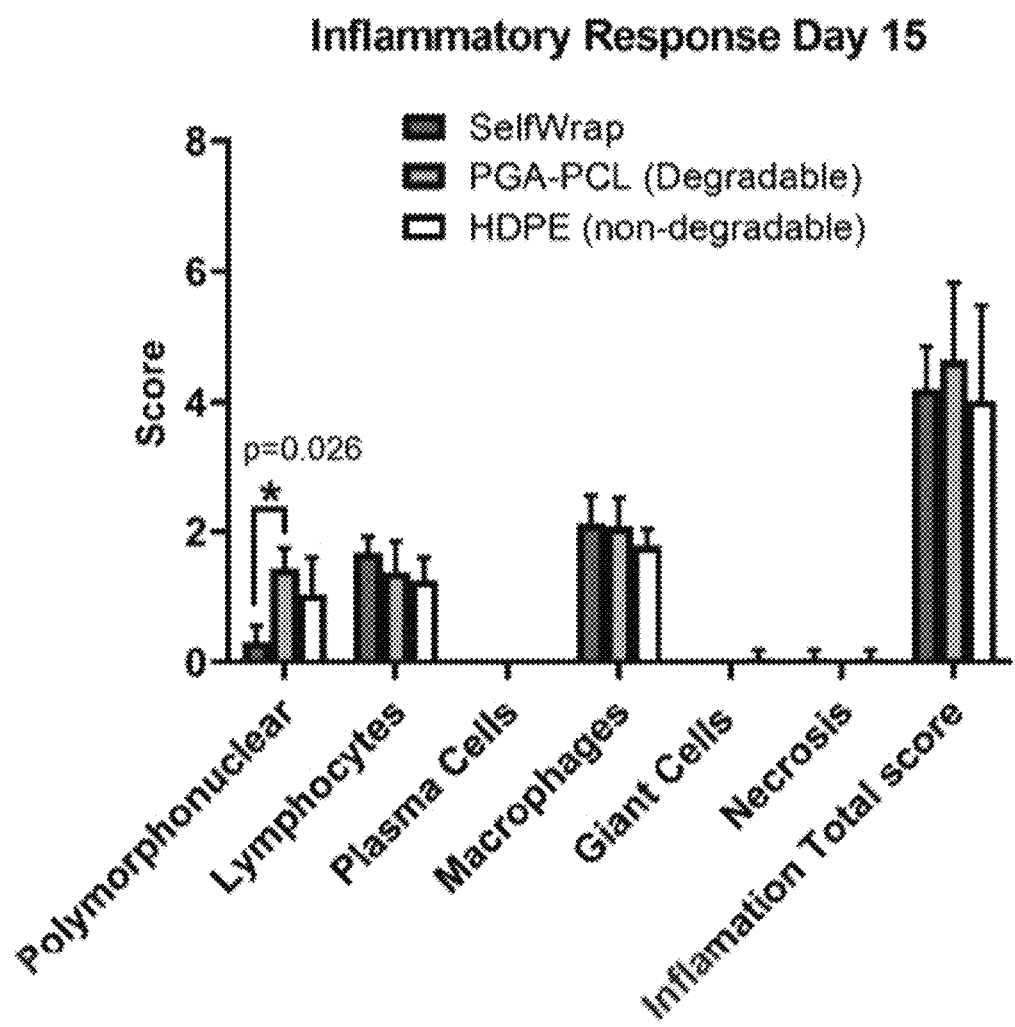
FIG. 10 is a graphical representation of data for inflammatory response at 15 days post-surgery.
Figure 11:
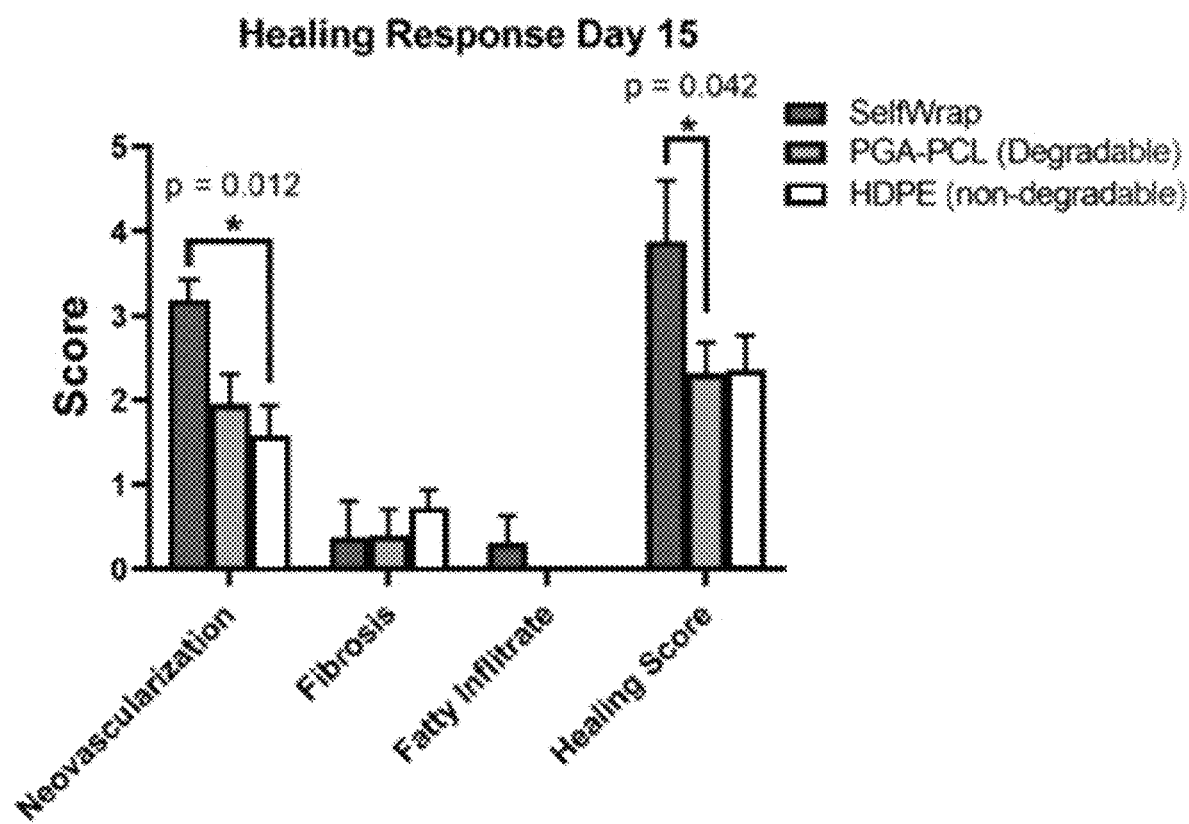
FIG. 11 is a graphical representation of data for healing response at 15 days post-surgery.

The bioreactivity score, which is a composite score calculated as twice the inflammation score (sum of polymorphs, lymphocytes, plasma cells, macrophages, giant cells, and necrosis) plus the healing score (neovascularization, fibrosis, and fatty infiltrate), was similar between the perivascular wrap, STRATAFIX®, and HDPE (FIG. 9). Inflammation score—the sum of inflammatory cells and necrosis—was also similar between all groups (FIG. 10). The only differences in inflammatory cell types were significantly fewer polymorphonuclear cells with the perivascular wrap compared to degradable PGA-PCL (p=0.026)—the lower score of polymorphs in the perivascular wrap compared to the nondegradable HDPE control was not significantly lower (p=0.20). The perivascular wrap group had a higher healing score than PGA-PCL (p=0.042, significant) and HDPE (p=0.055, not significant), due to more neovascularization (p=0.012 and 0.18 vs. PGA-PCL and HDPE, respectively) (FIG. 11). These results indicate greater neovascularization but similar bioreactivity for the perivascular wraps as disclosed herein compared to controls at 2 weeks.

Figure 12:
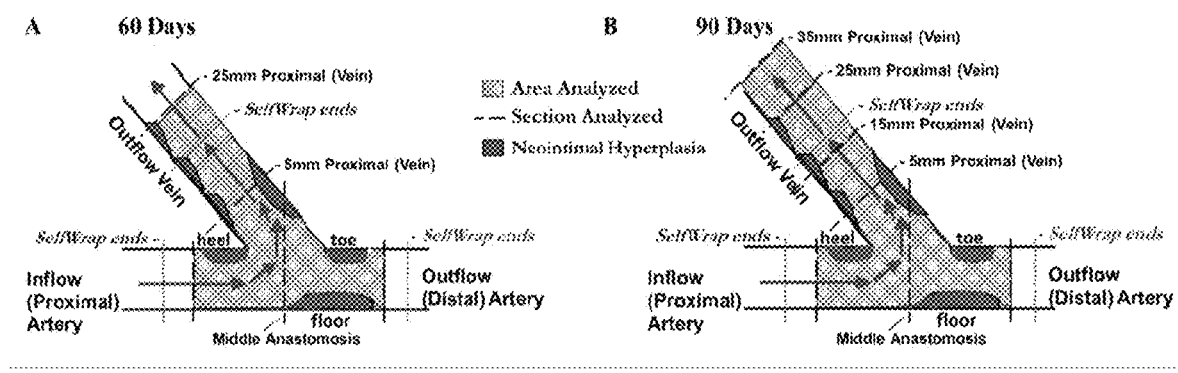
FIG. 12 is a graphical representation of the histological sections that were analyzed.

In some embodiments, the perivascular wraps as disclosed herein significantly reduce neointimal hyperplasia and increase lumenal area. A study was conducted where AVFs were created using femoral vein and artery as a model of human AVFs, with similar vessel sizes to the most prevalent brachiocephalic AVFs. In each animal, one randomly assigned AVF was treated with a perivascular wrap, and the other AVF was left as an untreated sham control. Angiography was used to assess blood flow and diameter of the AVF vessels bilaterally. Animals were then recovered and monitored throughout the remainder of the in-life period (6 sheep at 60±3 days, 8 sheep at 90±3 days). At the end of the survival period, angiography and ultrasound examinations were performed to assess the extent of AVF maturation. At the end of the study, arteries and veins of both AVFs (28 total) were explanted, stored in 10% neutral buffered formalin, and saved for histological evaluation (FIG. 12). Neointimal area and thickness are quantitative assessment of NH and were the primary endpoints, while secondary endpoints were % stenosis, lumen area, and medial area.

Figure 13:
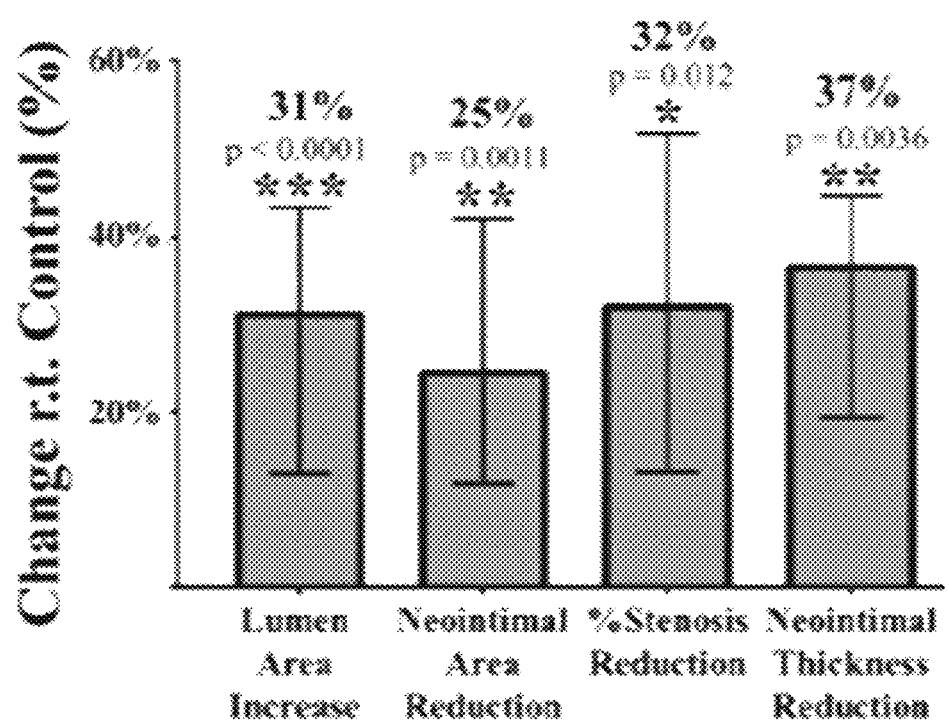
FIG. 13 is a graphical representation of data showing lumenal and neointimal area.
Figure 14:
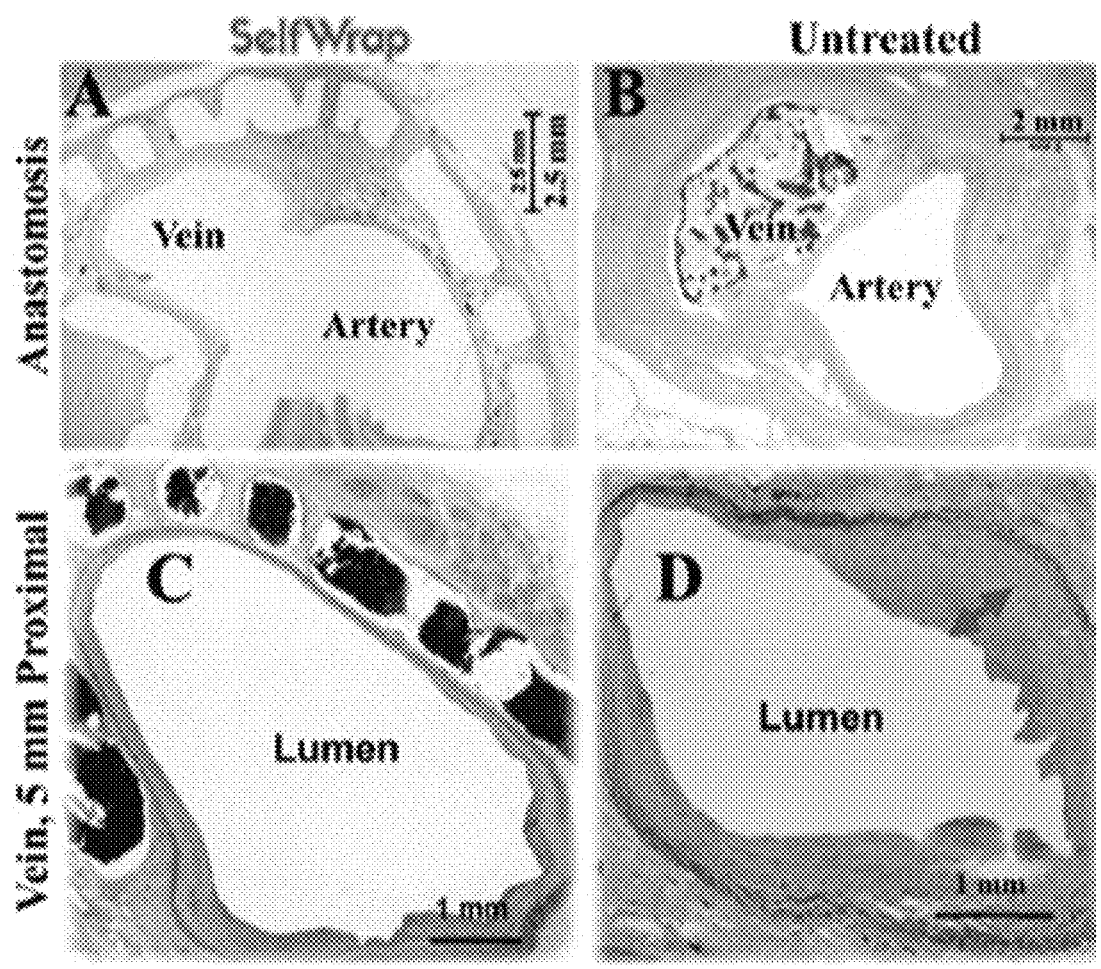
FIG. 14 is a representation of histological sections taken for treated and untreated sections.
Figure 15:
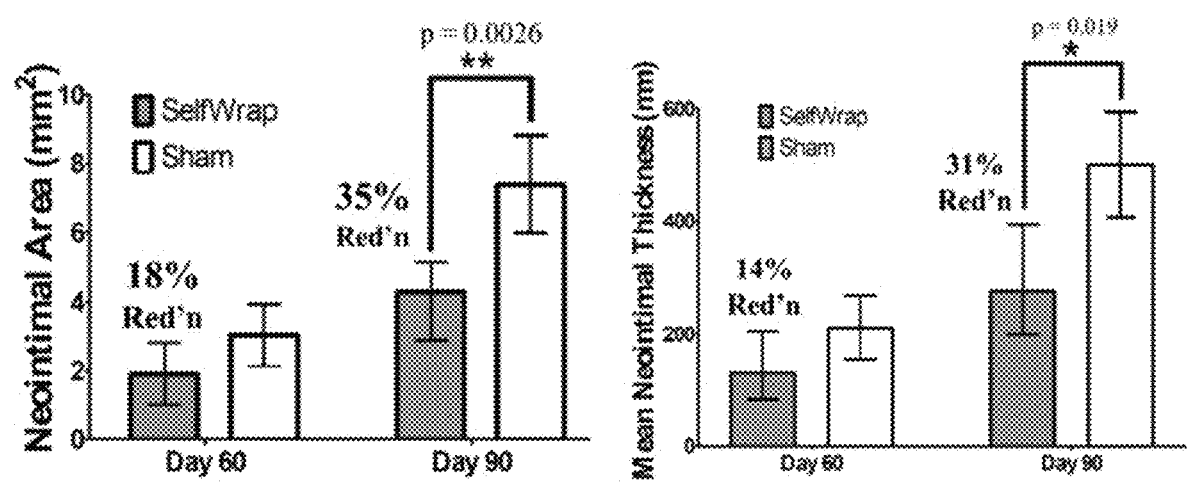
FIG. 15 is a graphical representation of data showing neointimal area and thickness of control and experimental groups.

The primary endpoints of neointimal area (p=0.0011) and thickness (p=0.0026), as well as secondary endpoint % stenosis (p=0.012), were significantly reduced by those with a perivascular wrap in a combined analysis of 60 and 90 day data for all anastomosis and vein sections (FIG. 13). Neointimal hyperplasia was reduced along both the anastomosis and vein with the perivascular wrap (FIG. 14); one control anastomosis sections was occluded at 90 days (FIG. 14, box B), whereas none of the AVFs with a perivascular wrap were. Neointimal area and thickness (FIG. 15), as well as medial area (FIG. 16), were especially reduced at 90 days, with 90-day p-values of 0.0026, 0.019, and 0.0016, respectively, and 90 vs. 60 day mean percent reductions of 35% vs. 18%, 31% vs. 14%, and 34% vs. 12%, respectively. These data indicate that the perivascular wrap reduces neointimal hyperplasia, improves patency and maturation, and reduces the incidences of stenosis, thrombosis, and CVC-related infections.

Figure 16:
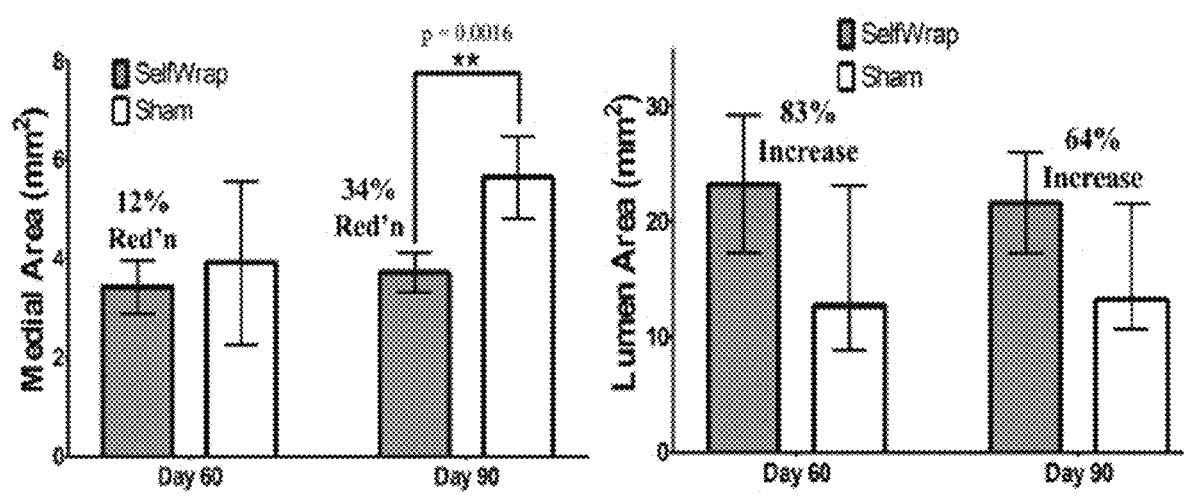
FIG. 16 is a graphical representation of data showing medial area and lumenal area of control and experimental groups.

There was also a significant increase in lumen area in the combined 60 and 90 day data for all anastomosis and vein sections (p<0.0001, FIG. 13). The 25-37% median improvements in the primary and secondary endpoints could not be explained by chance alone. Although the increases in lumen area over control at 60 and 90 days were not statistically significant when assessed separately via post-hoc Tukey's following two-way ANOVA, there were drastic mean differences in lumen area between perivascular wrap and control fistulas at 60 and 90 days: 83% and 64%, respectively (FIG. 16). Combined with the reductions in neointimal and medial areas, the perivascular wrap is inducing positive, outward vein remodeling, which further indicates superior maturation.

Figure 17:
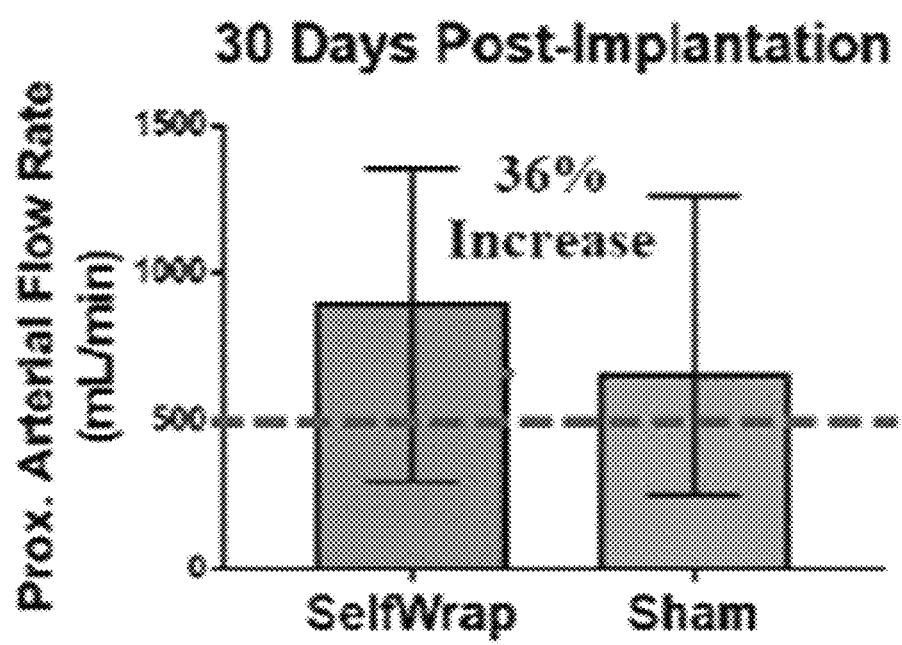
FIG. 17 is a graphical representation of blood flow rates at 30 days post-surgery.

Flow measurements at the second end (inflow) vessel can be considered clinically to be the best means of surveillance for a vascular access. Therefore, volumetric flow rates were a secondary endpoint of the study. Flow rates at 30 days <500 mL/min can be considered predictive of access dysfunction. At 30 days, there was a modest, 36% median increase inflow with perivascular wrap fistulas (FIG. 17), with 10/14 perivascular wrap fistulas above 500 mL/min compared to 8/14 sham, a 33% reduction in predictive access failures. Maturation success at 90 days, as defined by proximal arterial flow rates >500 mL/min and vein diameters >4 mm—was 75% (6/8) and 62.5% (5/8) for perivascular wrap-treated and non-treated sham fistulas, respectively. This data supports perivascular wrap-treated fistulas may improve maturation, and increase the maturation speed.

Figure 18:
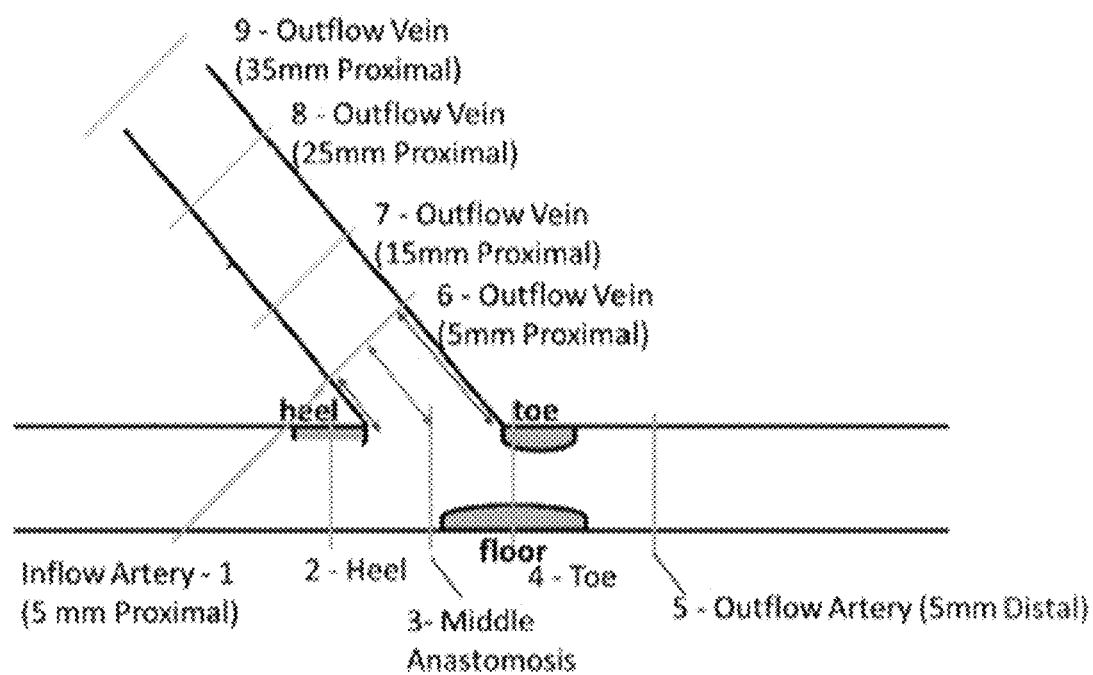
FIG. 18 is a graphical depiction of sections taken for analysis by microCT.

To evaluate in vivo degradation in the perivascular environment, microCT was performed on a paraffin-embedded tissue block from the 90-day sheep endpoint and from a paraffin-embedded block of a naïve perivascular wrap device. Both paraffin blocks were taken from cross sections 5 mm away from the anastomosis along both the inflow/proximal artery and outflow/proximal vein (FIG. 18), and processed in the same manner (i.e. fixed in formalin, washed in a series of graded alcohol washes to dehydrate, embedded in molten paraffin, and cooled to solidify the paraffin wax). Scans were done in a North Star Imaging (NSI) ×50 microCT machine and reconstructed at approximately 32 μm using the same settings for each scan. Three-dimensional volumes were sliced into 2D TIFF files and uploaded into 3D Slicer, where threshold segmentation and seed-based region growing algorithms were applied to delineate between the perivascular wrap device and surrounding tissue based on differences in pixel gray values. Volumes of the resulting segmentations was calculated and compared for the implant and the naïve perivascular wrap control.

Figure 3:
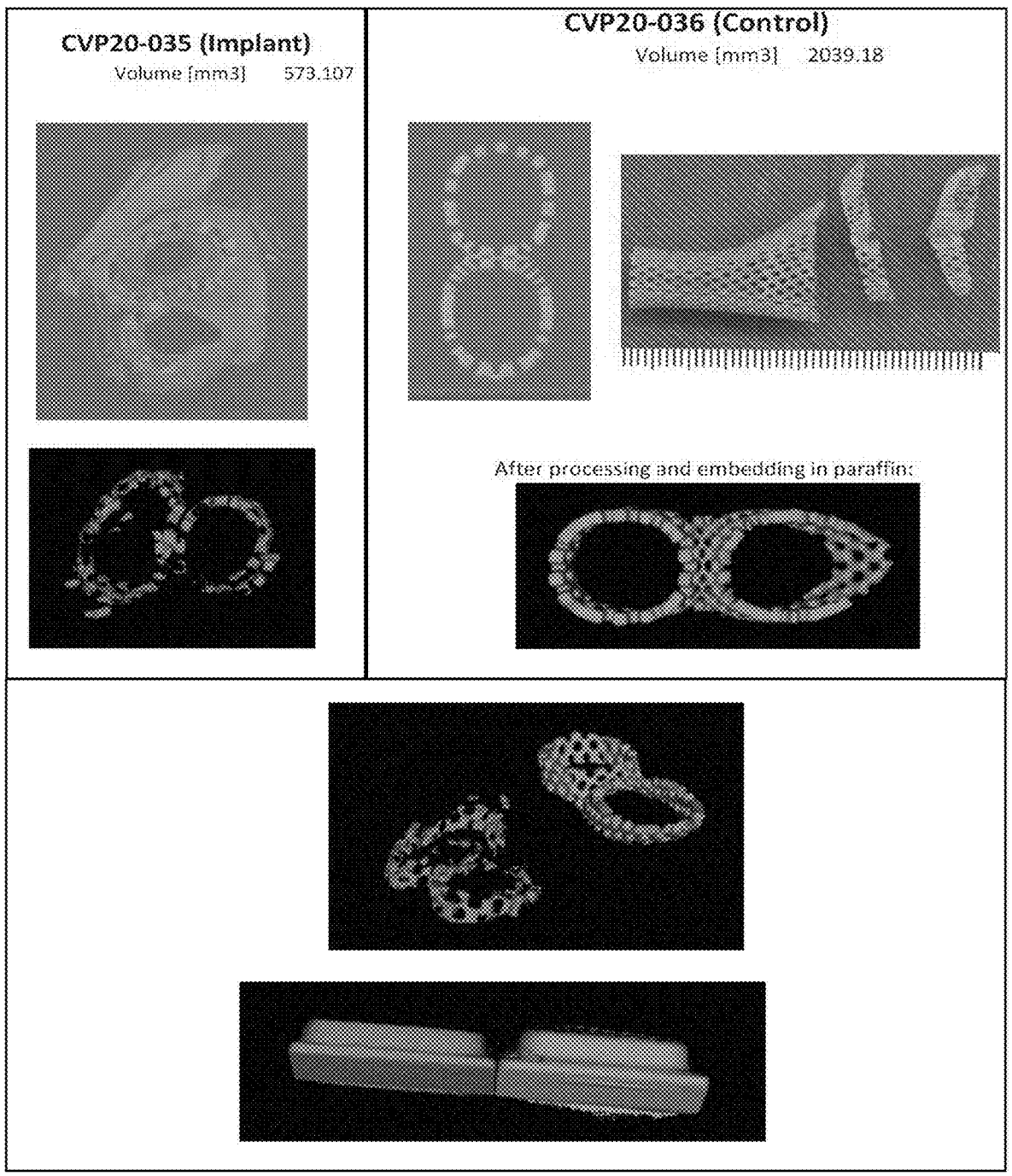
FIG. 3 is a MicroCT scan demonstrating lost volume and degradation in vivo.
Figure 19:
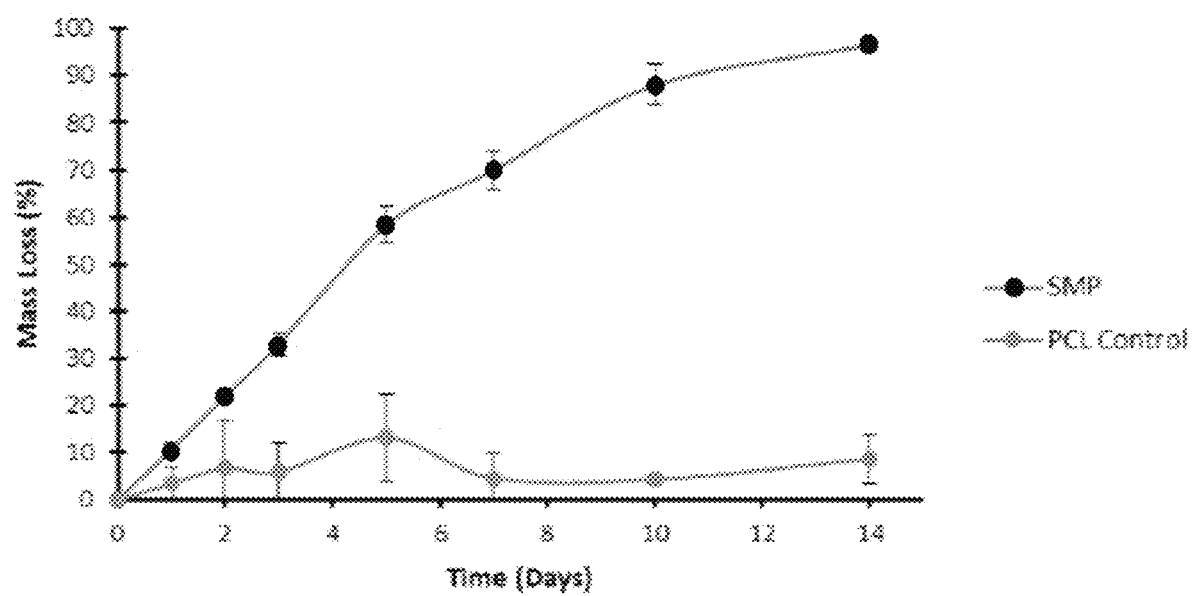
FIG. 19 is a graphical representation of data showing degradation rates.

Based on this assessment, it was estimated that the device was more than 50% degraded at 90 days (FIG. 3). This result is consistent with accelerated in vitro degradation studies of perivascular wraps. For this study, samples of the perivascular wrap device and a 10 kD crystalline PCL control were placed in separate vials and incubated in 0.5 M NaOH for 1, 3, 5, 7, 10, or 14 days (N=4 for each timepoint, for each group). Fresh 0.5 M NaOH medium was applied to each sample every 1-2 days. At each timepoint, samples were washed several times with deionized Milli-Q water to remove any salts, frozen overnight, and lyophilized for at least 24 hours. Samples were then weighed and vial weights subtracted to calculate % mass loss. Results are plotted (FIG. 19). Based on these results and PCL's known degradation time of 2-4 years, it was anticipated that the perivascular wraps of the instant application degrade within 6-12 months. It is estimated from in vitro and in vivo data that the perivascular wraps fully degrade within approximately 12 months.

Thus, although there have been described particular embodiments of the present invention of a new and useful SYNTHETIC PERIVASCULAR WRAP it is not intended that such references be construed as limitations upon the scope of this invention except as set forth in the following claims.

What is claimed is:

1. A method of treating an arteriovenous anastomosis, the method comprising the steps of:
    (a) determining the outer diameter of a first vessel to be surgically coupled to a second vessel creating a vascular anastomosis;
    (b) determining the outer diameter of the second vessel;
    (c) selecting a perivascular wrap such that the perivascular wrap envelops the arteriovenous anastomosis with a constriction of the first vessel of less than 30%; wherein the perivascular wrap includes a shape memory polymer and has at least a first end, a second end, and a medial region;
    (d) positioning the perivascular wrap onto the first vessel via the first end prior to construction of the arteriovenous anastomosis;
    (ε) coupling the first vessel and the second vessel constructing the arteriovenous anastomosis; and
    (f) molding the perivascular wrap from a first shape to a second shape wherein the second shape conforms to the geometry of the arteriovenous anastomosis such that the perivascular wrap comprises a first portion and a second portion, both the first and second portions proximate the second vessel wherein the first portion overlaps and adheres to the second portion creating a sutureless sheath about the second vessel, wherein a maximum principal strain of the first vessel is located at least 5 mm distally from a suture line of the first vessel to the second vessel, and wherein the perivascular wrap provides artery-mimetic support to the arteriovenous anastomosis in the range of 0.1-2.0 MPa.

2. The method of claim 1 wherein the first vessel comprises a vein.

3. The method of claim 1 wherein the second vessel comprises an artery.

4. The method of claim 1 wherein the determining step of (a) includes measuring the outer diameter via ultrasound.

5. The method of claim 1 wherein the determining step of (b) includes measuring the outer diameter via ultrasound.

6. The method of claim 1 further comprising determining the inner diameter of the first vessel.

7. The method of claim 1 further comprising determining the inner diameter of the second vessel.

8. The method of claim 1 wherein the shape memory polymer comprises poly (ε-caprolactone).

9. The method of claim 1 wherein the shape memory polymer comprises poly (ε-caprolactone)-co-(α-allyl carboxylate ε-caprolactone).

10. The method of claim 1 wherein the molding of the perivascular wrap is formed to have direct contact with the outer walls of the first and second vessels of the anastomosis.

11. The method of claim 1 wherein the first end is tapered away from the medial region such that a diameter of the first end at a distal end from the medial region is larger than a diameter of the first end at a proximal end of the medial region.

12. A method of treating an arteriovenous anastomosis, the method comprising the steps of:
    (a) coupling a first vessel and a second vessel to construct the arteriovenous anastomosis;
    (b) providing a perivascular wrap;
    (c) contacting the perivascular wrap to the arteriovenous anastomosis after the construction of the arteriovenous anastomosis;
    (d) molding the perivascular wrap from a first shape to a second shape wherein the second shape conforms to the geometry of the arteriovenous anastomosis such that the perivascular wrap comprises a first portion and a second portion, both the first and second portions proximate the second vessel wherein the first portion overlaps and contacts the second portion creating a sutureless sheath about the second vessel, wherein a maximum principal strain of the first vessel is located at least 5 mm distally to a suture line of the first vessel to the second vessel, and wherein the perivascular wrap provides artery-mimetic support to the arteriovenous anastomosis in the range of 0.1-2.0 MPa.

13. The method of claim 12 wherein the first vessel comprises a vein.

14. The method of claim 12 wherein the second vessel comprises an artery.

15. The method of claim 12 wherein the shape memory polymer comprises poly (ε-caprolactone).

16. The method of claim 12 wherein the shape memory polymer comprises poly (ε-caprolactone)-co-(α-allyl carboxylate ε-caprolactone).

17. The method of claim 12 wherein the molding of the perivascular wrap is formed to have direct contact with the outer walls of the first and second vessels of the anastomosis.

18. The method of claim 12 wherein the first end is tapered away from the medial region such that a diameter of the first end at a distal end from the medial region is larger than a diameter of the first end at a proximal end of the medial region.

* * * * *